United States Patent [19]

Schelhas

[11] Patent Number: 4,822,370
[45] Date of Patent: Apr. 18, 1989

[54] HIP JOINT FEMORAL PROSTHESIS

[75] Inventor: Klaus-Dieter Schelhas, Bremem, Fed. Rep. of Germany

[73] Assignee: Orthoplant Endoprothetik, Bremen, Fed. Rep. of Germany

[21] Appl. No.: 210,200

[22] Filed: Jun. 20, 1988

Related U.S. Application Data

[63] Continuation of Ser. No. 115, Jan. 2, 1987, abandoned.

[30] Foreign Application Priority Data

Jan. 14, 1986 [DE] Fed. Rep. of Germany ....... 3600804

[51] Int. Cl.$^4$ ................................. A61F 2/36
[52] U.S. Cl. .......................... 623/23; 623/18
[58] Field of Search ........................ 623/23, 22, 18, 16

[56] References Cited

U.S. PATENT DOCUMENTS

| | | | |
|---|---|---|---|
| 3,722,002 | 3/1973 | Charnley | 623/22 |
| 4,031,570 | 6/1977 | Frey | 623/22 |
| 4,578,081 | 3/1986 | Harder et al. | 623/22 |
| 4,608,055 | 8/1986 | Morrey et al. | 623/23 |

FOREIGN PATENT DOCUMENTS

| | | | |
|---|---|---|---|
| 2646842 | 4/1978 | Fed. Rep. of Germany | 623/23 |
| 2734249 | 2/1979 | Fed. Rep. of Germany | 623/23 |
| 3340767 | 5/1985 | Fed. Rep. of Germany | 623/22 |
| 2580926 | 10/1986 | France | . |

Primary Examiner—Ronald L. Frinks
Attorney, Agent, or Firm—Merchant, Gould, Smith, Edell, Welter & Schmidt

[57] ABSTRACT

Given a hip joint femoral prosthesis having a shaft, a spherical head and a connecting part between the shaft and the head. Disposed at the proximal end of the shaft and in the head in each case is a conical boring. Located at the shaft side end and at the head side end of the connecting part is a socket cone cooperating with each conical boring. The longitudinal axis of the first socket cone and the longitudinal axis of the second socket cone of the connecting part intersect at a predetermined angle $0 \leq \beta \leq 50°$ (zero is less than or equal to beta and beta is less than or equal to 50°), in order to be able to adapt better the relative position of the head to the shaft, individually, to the conditions of the patient.

5 Claims, 2 Drawing Sheets

HIP JOINT FEMORAL PROSTHESIS

This is a continuation, of application Ser. No. 000,115, filed Jan. 2, 1987, now abandoned.

TECHNICAL FIELD

The invention concerns a hip joint femoral prosthesis.

BACKGROUND OF THE INVENTION

Known from the German Laid Open Print 27 34 249 is a hip joint acetabular prosthesis of this type where the connecting part forms a single-piece head part with the spherical head and displays at its shaft side end a socket cone capable of being pushed into and fixed in a corresponding conical boring of the shaft. This known two-part construction of head and shaft has the advantage of a flexible adaptation of head size and shaft size to the patient data, with a comparably surveyable inventory. If certain shaft sizes and head parts are kept ready, the operator can then select, even during the operation, rapidly the suitable head and shaft combination. Additionally, the head part, consisting of head and connecting part, can be aligned independently of the final position of the shaft and then fixed.

Besides shaft size and head size, still further strongly patient-dependent, as a rule, is the so-called CCD-angle that the shaft axis forms with the shank neck axis running through the head center point and the adjacent shank neck, and crossing the shaft axis. This CCD-angle in the case of the natural femur on the average lies at approximately 126°, with a width of variation between 115° and 140°. In the case of the two-piece hip joint acetabular prosthesis in accordance with the German Laid Open Print 27 34 249, the CCD-angle is obtained by approximate curving of the single-piece connecting part formed at the head; the selection of a suitable CCD-angle and the selection of a required head size that is independent thereof is, therefore, not possible in the case of this known hip joint femoral prosthesis. A somewhat sufficient adaptation of CCD-angle and head size to the patient data, much more to the point, can, in the case of this known hip joint femoral prosthesis, only be realized by maintaining in stock (inventory) for each head size a plurality of head parts with different CCD-angles. Therefore, the operator must, e.g. during an operation, select from a large number of different head parts the one displaying the correct head size and, additionally, the correct CCD-angle.

Known from the German Laid Open Print 33 40 767 is an assembly made up of several piece parts that can be put together into a hip joint acetabular prosthesis of desired length, whereby the piece parts inserted between the shaft and the head each display, on the shaft side, a conical boring and, on the head side, each a corresponding conical stub in order to enable a simple assembly of the hip joint femoral prosthesis. The task set forth for the invention is to further develop the hip joint femoral prosthesis of the initially mentioned art such that adaptation of the CCD-angle of the femoral prosthesis to patient requirements is possible in simple fashion, independently of the selected size of prosthesis head and of prosthesis shaft.

This task is resolved in the present case of the hip joint femoral prosthesis.

The advantages of the invention lie, in particular, in the fact that the hip joint femoral prosthesis has, between the shaft and the head, a separate connecting part that serves for realizing the patient-correct, desired CCD-angle and, additionally, enables a linkage-correct alignment of the head by appropriate rotation of the connecting part in the conical boring of the shaft, and subsequent fixing. By suitable selection of shaft size, of the angled connecting part and of the head size, capable of being realized is a hip joint femoral prosthesis that is easily adaptable to the individual patient data, if these three parts are stocked in appropriately sized steps. By this means, inventory remains capable of being surveyed, and the selection of the parts required for realizing the individually fitted femoral prosthesis is relatively surveyable and simple for the operator-even during an operation.

Advantageously, the two socket cones have, at both ends of the connecting part, the same dimensions and the conical borings at the proximal end of the shaft, respectively in the head, are then likewise constructed the same, so that mixing up the socket cones leads to no problems.

Particularly preferred, the conical boring in the proximal end of the shaft runs at a predetermined angle of $\alpha$(alpha)$< 180°$ to the shaft axis, with the conical boring then being made in a region of the shaft that retains about the conical boring the greatest possible wall thickness and, therewith, the greatest possible wall strength. With this form of embodiment of the invention, the CCD-angle is obtained by the difference between the angle and $\beta$ (beta). Particularly preferred, the conical boring of the shaft runs at an angle $\alpha \approx 140°$ (alpha approximately equal) to the shaft axis, and the angle $\beta$ (beta) between the two socket cones of the connecting part then lies, for realizing a CCD-angle of 140° to 110°, in the region of $0 \leq \beta \leq 30°$ (zero is less than or equal to beta and beta is less than or equal to 30°).

BRIEF DESCRIPTION OF THE DRAWINGS

Explained in more detail in the following with the aid of the drawing are some examples of embodiment of the invention. Shown are.

DETAILED DESCRIPTION OF THE INVENTION

Figure 1:
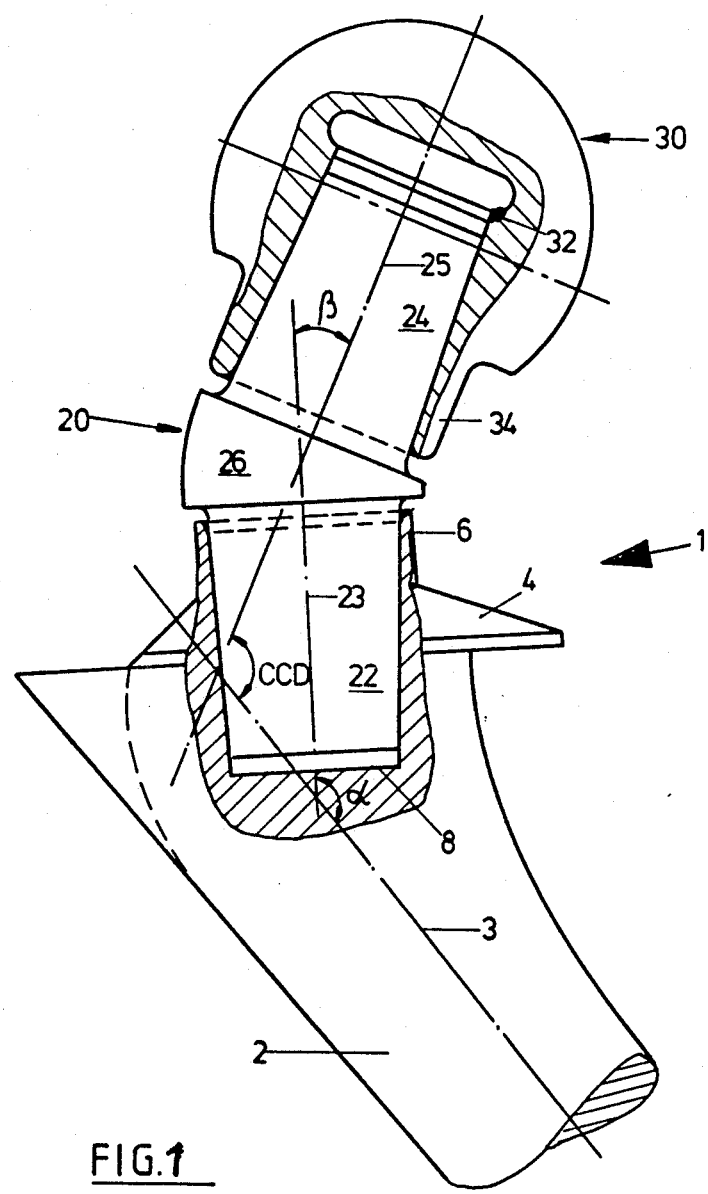
FIG. 1 is a hip joint femoral prothesis with a connecting part between the head and the shaft.

The hip joint femoral prosthesis 1 represented in FIG. 1 has a shaft 2, the distal end of which is broken away and whose proximal end has a surrounding collar 4 and a neck section 6 formed on the collar 4. Worked into the shaft 2, from the shaft side neck section 6, is a conical boring 8 whose axis 23 coincides with the axis of the neck section 6, and which, with the shaft axis 3, includes an angle $\alpha$ (alpha).

Inserted, while forming a firm frictional connection, into the conical boring 8 at the proximal end of the shaft 2 is a first socket cone 22 that is disposed on the shaft side end of a connecting part 20. Adjoining at the socket cone 22 of the connection part 20 is a center section 26 and, thereupon, a second socket cone 24 that represents the head side end of the connecting part 20 and that is capable of being anchored in a conical boring 32 in the head 30. The center section 26, together with the neck section 6 of the shaft 2, represents the hip joint femoral prosthesis and is constructed essentially cylindrically. Axis 25 running through the second socket cone 24 and the center point of the head 30 intersects with axis 23 of the first socket cone 22 and, with this axis 23, includes an angle β (beta) lying approximately between 0° and 50°. The first socket cone 22 is capable of being inserted into and anchored in conical boring 8 in the shaft 2 at any angular position relative to shaft 2 so that the shaft 2 through the connecting part 20 to the head 30 can undergo two angular deflections.

The shank neck axis 25 running through the central section 26 and the middle point of head 30 cuts the shaft axis 3 at the CCD-angle for which applies, for the form of embodiment represented:

$$\text{CCD-angle} = \alpha - \beta \text{ (alpha minus beta)}$$

The spherical head 30 passes over at one point of its surface into a cylindrical neck section 34, into which is worked the conical boring 32, whose axis 25 is identical with the axis of the neck sectiion 34 and that runs through the middle point of the head 30. The two end side socket cones 22, 24 of the connecting part 20 and, therewith, subsequently also the conical borings 8 and 32, have the same dimensions. The head 30 is plugged on over the second socket cone 24.

The socket cones 22, 24 and the conical borings 8, 32 are dimensioned such that there remains a predetermined small axial interval between the neck section 6 of the shaft 2, respectively the neck section 34 of the head 30, and the central section 26 in order, if required, to be able to insert a tool for loosening the socket cone connections. The socket cones 22, 24 pass over in rounded fashion into the center section 26 of the connecting part 20, which is constructed as a rotating bulge.

In the form of embodiment represented, the angle α (alpha) between shaft axis 3 and axis 23 of the conical boring 8 comes to about 140°, the angle β (beta) between the longitudinal axes 23 and 25 of the two socket cones 22 and 24 comes to about 25°, the CCD-angle between the conical axis 25 and the shaft axis 3 comes then to about 115°.

Figure 2C:
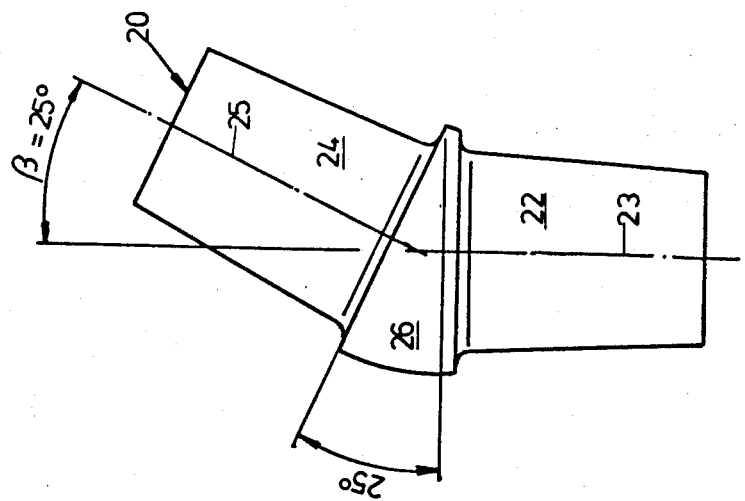
FIGS. 2a, 2b and 2c are side views of differently angled connecting parts.
Figure 2B:
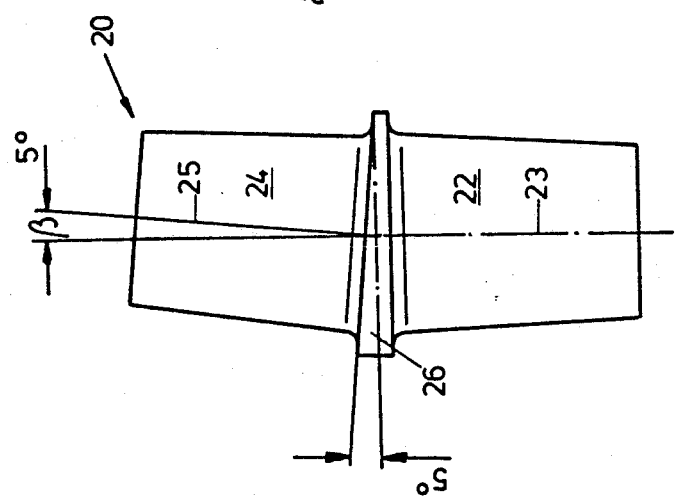
Figure 2A:
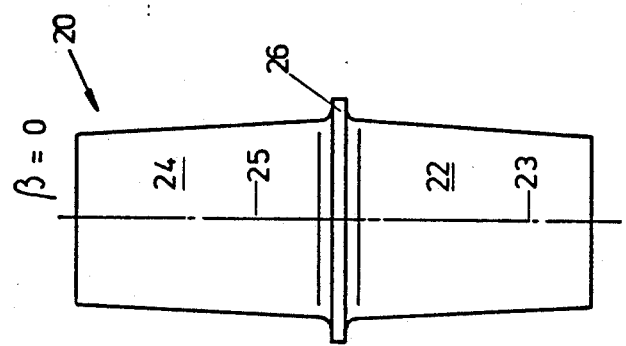

Represented in FIG. 2 are different connecting parts 20 having a different angle β (beta) between the longitudinal axes 23, 25 of the socket cones 22, 24. The connecting part in accordance with FIG. 2a has an angle β (beta)=0, the head then sits aligned straight over the socket cone 22, the CCD-angle is identical with angle α (alpha) and then comes to about 140° in the case of the shaft represented.

Represented in FIG. 2b and 2c are connecting parts 20 whose angles β (beta) between the longitudinal axes 23, 25 of the socket cones 22, 24 come to 5°, respectively 25°.

I claim:

1. Hip joint femoral prosthesis comprising a shaft, a spherical head and a connecting part between the shaft and the head, with a conical boring at the proximal end of the shaft and a corresponding first socket cone on the shaft end of the connection part, and wherein the connecting part displays on the head end a second socket cone, wherein said first socket cone is capable of being inserted into and anchored in a conical boring in the shaft at any angular position relative to said shaft, and that the longitudinal axis of the first socket cone and the longitudinal axis of the second socket cone intersect at a predetermined angle $0° \leq \beta \leq 50°$ (zero is less than or equal to beta and beta is less than or equal to 50°) so that from the shaft through the connecting part to the head may undergo two angular deflections.

2. Hip joint femoral prosthesis according to claim 1, wherein the connecting part between the two socket cones displays a center section that is constructed as a rotating bulge.

3. Hip joint femoral prosthesis according to claim 1 wherein the two socket cones of the connecting part and the conical boring located in the shaft, respectively in the head display the same dimensions.

4. Hip joint femoral prosthesis according to claim 1, wherein the conical boring of the shaft runs at a predetermined angle $\alpha < 180°$ (alpha is less than 180°) to the shaft axis.

5. Hip joint acetabular prosthesis according to claim 4, characterized by the fact that the angle α (alpha) is about 140°.

* * * * *